Figure 1:
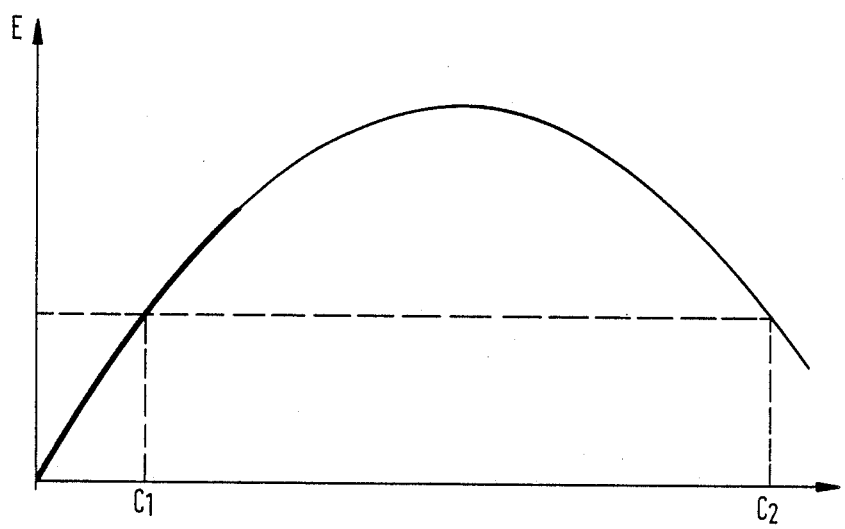

United States Patent [19]

Kaspar

[11] Patent Number: 4,966,839
[45] Date of Patent: Oct. 30, 1990

[54] PROCESS FOR THE DETERMINATION OF AN IMMUNOLOGICALLY BINDABLE ANALYTE

[75] Inventor: Klaus P. Kaspar, Asuncion, Paraguay

[73] Assignee: Boehringer Mannheim GmbH, Mannheim, Fed. Rep. of Germany

[21] Appl. No.: 317,111

[22] Filed: Feb. 28, 1989

Related U.S. Application Data

[63] Continuation of Ser. No. 926,641, Nov. 3, 1986, abandoned.

[30] Foreign Application Priority Data

Nov. 5, 1985 [DE] Fed. Rep. of Germany ....... 3539215

[51] Int. Cl.$^5$ .................. G01N 33/53; G01N 33/557; G01N 33/543; G01N 33/542
[52] U.S. Cl. ......................................... 435/7; 435/176; 436/501; 436/513; 436/517; 436/518; 436/524; 436/528; 436/537; 436/540; 436/819; 436/824; 530/810
[58] Field of Search .................. 435/7, 181, 6, 176; 436/512, 513, 517, 524, 528, 532, 537, 540, 819, 501, 518, 824; 530/810

[56] References Cited

U.S. PATENT DOCUMENTS

| | | | |
|---|---|---|---|
| 4,381,291 | 4/1983 | Ekins | 436/518 X |
| 4,459,359 | 7/1984 | Neurath | 436/530 X |
| 4,462,964 | 7/1984 | Gaigan | 422/102 |
| 4,595,661 | 6/1986 | Cragle et al. | 436/518 X |
| 4,673,653 | 6/1987 | Gaigan | 422/56 X |
| 4,690,899 | 9/1987 | Klose et al. | 436/45 |

*Primary Examiner*—Esther L. Kepplinger
*Assistant Examiner*—Florina B. Hoffer
*Attorney, Agent, or Firm*—Felfe & Lynch

[57] ABSTRACT

The present invention provides a process for the determination of a bindable analyte according to the principle of heterogeneous immunoassay by incubation of a sample solution which contains the analyte with a labelled first receptor specifically bindable with the analyte and present in dissolved phase and a second receptor present in a solid phase which does not cross-react with the first receptor and can fix a complex which contains the analyte and first receptor, separation of the phases after incubation and quantitative measurement of the labelling bound to the solid phase, wherein there is determined the back dissociation velocity of the labelling bound to the solid phase into the dissolved phase and the quotients of the back dissociation velocity and measurement value are used as a measure for the correctness of the test result of the first measurement.

8 Claims, 2 Drawing Sheets

PROCESS FOR THE DETERMINATION OF AN IMMUNOLOGICALLY BINDABLE ANALYTE

This application is a continuation, of application Ser. No. 926,641, filed Nov. 3, 1986 now abandoned.

The present invention is concerned with a process and a reagent for the determination of a bindable analyte according to the principle of the two-side heterogeneous immunoassay.

Two-sided immunoassays (sandwich tests) show marked advantages with regard to exactitude, sensitivity and rapidity as compared to competitive immunoassays. When the concentration of reagent, material used for the assay, or sample varies, the measurement value for the assay reaches, and passes through a maximum value. This effect is called the hook effect. For sandwich assays involving a solid phase, as analyte concentration increases, the measurement signal first increases, and reaches a maximum. As analyte concentration increases further, however, the measurement signal decreases. In this case, the same result can be brought about by two different amounts of analyte (see FIG. 1 of the accompanying drawings). This effect, which is dependent upon the amount of analyte, is called the "high dose" hook effect and limits the use of sandwich assays in spite of the above-mentioned advantages.

Various reasons are given for the hook effect, such as heterogeneity of the antibodies present in the receptors or incomplete washing (see D. Rodbard et at., Immunochemistry, 15, 77—82/1978). Additionally, theoretical considerations lead to the conclusion that the hook effect must occur for all one-step sandwich tests. As one-step tests are meant all tests in which the analyte is brought to reaction with two receptors specific for it in the same solution and thereby or subsequently is fixed to an insoluble carrier material. This is in contrast to sequential assays where, after reaction of the analyte with a first specific receptor and fixing of the complex formed on to a solid phase, non-bound analyte is removed by washing the solid phase before reacting the complex with a second specific labelled receptor. In the case of the one-step sandwich test, the hook effect automatically occurs when both specific receptors are present in an insufficient amount with respect to the analyte so that only a part of the analyte is complexed with conjugate and also only a part of these complexes is fixed to the solid phase.

All protein determinations with the help of a third'-'catching" receptor, involving complexing of two soluble receptors with the analyte and solid phase fixation via a further receptor, are also, in the above sense, one-step tests and display a hook effect. This can, inter alia, in the case of tumour markers, for example AFP, CEA, hCG, IgE etc., simulate results in the normal range in the case of already highly pathological samples. Therefore, for medical determinations, the use of the one-step sandwich process is frequently not used as a matter of principle. A recognition of such measurement results which simulate false values due to the hook effect is an important advance since all advantages of the onestep sandwich method (shortening of the reaction time, sensitivity, exactitude, etc.) could be utilized without the risk of a false result due to the hook effect having to be taken into account.

K.L. Hoffmann et al. (Clinical Chemistry, 30 (9), 1499/1984) describe that a number of experiments have been carried out in order to prevent the appearance of the hook effect. Thus, for example, a stepwise analysis is suggested in which the analyte is first reacted with a receptor on the solid phase. Following this, the solid phase is then extensively washed, and this washing step is followed by a second incubation with soluble labelled receptor. Finally, the solid phase is washed a second time in order to separate the bound labelled receptors from the unbound ones. Furthermore, a reduction of the sample size, the carrying out of the test with various dilutions of the analyte or the use of only a small range of the calibration curve are suggested. The use of labels with low activity is also recommended, in order to allow the use of high concentrations of labelled receptors without the activity (radio, fluorescence, enzyme or colour forming activity) becoming too large.

In addition, Hoffmann et al. (loc. cit.) describe a determination process for a one-step sandwich test in which the increase of the part lining to the solid phase of the labelled receptor is monitored kinetically and these values are fed into a computer, the reaction velocities then being calculated. Measurement results which have been brought about by the hook effect can thereby be differentiated from other values in that they display substantially smaller increases in complex binding. This process suffers from the disadvantage that extremely laborious and expensive computer processes have to be used in order to recognize whether a hook effect is present. Furthermore, this process is unsuitable for enzyme immunological determinations.

Therefore, it is an object of the present invention to provide a process in which false measurement results brought about by the hook effect can be easily recognised without the inherent disadvantages of the known processes. These disadvantages include loss of sensitivity and loss of precision as well as increasing the amount of work, reagent and apparatus needed.

Thus, according to the present invention, there is provided a process for the determination of a bindable analyte according to the principle of hetergeneous immunoassay by incubation of a sample solution which contains the analyte with a labelled first receptor specifically bindable with the analyte and present in dissolved phase and a second receptor present in a solid phase which does not cross-react with the first receptor and can fix a complex which contains the analyte and first receptor, separation of the phases after incubation and quantitative measurement of the labelling bound to the solid phase to obtain a first measurement, wherein there is determined the back dissociation velocity of the labelling bound to the solid phase into the dissolved phase and the quotients of the back dissociation velocity and measurement value are used as a measure for the correctness of the test result of the first measurement.

In the usual sandwich test, after separation of the sample and reagent liquid, the solid phase-fixed sandwich complexes are determined via the amount of bound labelled receptors (radioactive, enzymatic, fluorometric or similarly labelled). Due to this separation and removal of non-bound labelled receptor, the equilibrium of the analyte-receptor binding is destroyed and a back dissociation of the sandwich components commences. This results in the presence of non-solid phase-fixed labelled receptor molecules in the liquid phase. The degree of back dissociation can be determined by determination of the labelling in the solid or separated liquid phase. As liquid phase, there can be used, for example, the wash liquid and, in the case of enzyme immunoassays, the substrate solution for the enzyme determination. In this substrate solution, according to the present invention, there is first determined the measurement value resulting at the point of time of the phase separation (colour signal) and subsequently the kinetics of the further colour formation are determined to measure back dissociation of the label.

Since the liberation of an amount of label caused by back dissociation of the analyte-receptor complex proceeds approximately as a reaction of the first order, it is proportional to the amount of analyte and to the measurement signal associated therewith. Thus, the liberated amount of label can be expressed by a quotient alpha, which is the change of the measurement value after phase separation per unit time divided by the measurement value. Surprisingly, when a hook effect occurs, the quotient alpha is markedly changed in comparison with cases in which no hook effect occurs.

Thus, with the help of the quotient alpha, it can be decided whether a measurement value obtained with the help of a calibration curve may be recalculated into an amount of analyte or whether the measurement value has been produced by a hook effect. In this case, it must be concluded that the sample contains an amount of analyte above the uppermost standard.

In the scope of the process according to the present invention, analyte and receptor can, in principle, be all substance pairings which are bindable with one another. In this definition are included, from immunologically bindable substance pairs, and substance pairs which behave in an analogous manner. Besides the substance pair antigen-antibody, which first comes into consideration and is preferably used, (the term antibody here includes also known immunologically active fragments, not only of polyclonal but also of monoclonal origin), examples of substance pairs include protein A-immunoglobulin G, avidin-biotin, concanavilin A-lectin, as well as DNA-RNA (hybrid binding). All these substance pairs can be determined according to the principle of heterogeneous immunoassay (sandwich test) with one-step incubation according to the process of the present invention.

As receptors, in the scope of the present invention, there are included the components of the above-mentioned specifically bindable substance pairs or derivatives thereof, especially the derivatives of bindable substances frequently referred to as conjugates, which are formed by covalent binding to a label molecule. An example of such a receptor, preferred in the scope of the present invention and which is present as conjugate, is an antibody or antibody fragment which is covalently bound with a labelling enzyme. However, instead of a labelling enzyme, there can also be used dyestuff molecules, colour forming components, especially fluorescent dyestuff molecules and the like as substance suitable for a detection system. Such a conjugate can also be radioactively labelled.

Alternatively, the antibody itself can also contain radioactive atoms as label. In this case, the labelled first receptor consists, for example, of a radioactive antibody.

The second receptor bound to the solid phase can also consist of a partner of the above-mentioned bindable substance pairs as such or a derivative thereof. The solid phase-bound second receptor serves, in the case of the sandwich assay, to fix the complex of analyte and first receptor to a solid phase and thus to make it easily separable from the liquid phase. For this purpose, the second receptor can bind directly with the analyte to be determined. In this case, the second receptor is directed against a determinant of the analyte other than that of the first receptor and, consequently, preferably consists of a monoclonal antibody or a fragment thereof. However, the second receptor can also be directed against another determinant of the complex of analyte and first receptor not present on the analyte itself. In this case, there is preferably also used a third receptor which is also specific for the analyte and recognises a determinant other than that recognised by the first receptor. Analyte, first receptor and third receptor then for a complex and, in this case, as second receptor, there is preferably used an antibody which binds with the third receptor. In an especially preferred embodiment, the first specific receptor contains an antibody fragment, especially a Fab fragment, and the third receptor consists of a complete antibody. In this case, the third receptor and the antibody part of the first receptor are monoclonal. The second receptor is, in this case, preferably directed against a part of the third receptor and especially preferably against the Fc part of the third receptor when the first receptor contains a Fab fragment. It is also possible to derivatise the third receptor and to use a second receptor which is directed against this derivatised place.

The back dissociation velocity of the solid-phase bound label, which is important for the process according to the present invention, is determined by the binding strength between a receptor directed against the analyte and the analyte itself. According to a preferred embodiment of the present invention, the back dissociation constant for at least one analyte concentration is adjusted to an average value, i.e. one that is neither too high or too low a back dissociation velocity. If the velocity is too high, then the measurement intervals are, of necessity, ever smaller, which results in inexactitudes. Too low a dissociation velocity considerably increases the time necessary for carrying out the process and makes difficult the recognition of a reduced back dissociation rate such as occurs in the case of the presence of the hook effect. Since the process is preferably carried out in conventional automatic analysers, the capacity of the automatic devices can then no longer be fully utilised.

As average back dissociation velocity, there is to be understood one which makes possible a measurement interval of from about 20 seconds to 60 minutes. A dissociation velocity in this range can be achieved by appropriate choice of the binding strength between a receptor and its binding partner, the analyte. For example by appropriate choice of the binding strength of the antibody, and/or by the binding strength-influencing additives in the reaction medium, such as surfaceactive substances and salts may be made. For this purpose, there are especially used detergents and/or chaotropic ions. Preferably, the various components and the intended measurement time period are so adjusted with regard to one another that at least, at one analyte concentration, within the period of time (measurement interval), at least 10% of the labelling bound to the solid phase again dissociates off.

In the case of the preferred embodiment of the present invention with the use of an enzyme-labelled first receptor, after incubation of all components and separation of the phases, the separated solid phase is preferably incubated with a solution of a colour reagent for the determination of the labelling enzyme. Subsequently the colour reagent solution is separated from the solid phase and in the separated solution the back dissociation constant is determined by at least two measurements at a definite time interval. This embodiment is based upon the fact that, during the contact between the colour reagent solution and the solid phase, the total amount of the labelling enzyme bound to the solid phase and labelling enzyme possibly dissociated off during this incubation contribute to the colour formation. After phase separation, further color formation takes place which is only to be attributed to the dissociated-off labelling enzyme. The dissociated-off amount of the labelling enzyme (which corresponds to the dissociated-off amount of complex of analyte and first receptor) can, therefore, easily be determined by two measurements.

According to a further embodiment of the present invention, after the first phase separation, the solid phase is incubated with a liquid phase, rather than a substrate solution (e.g. enzyme labeled). After a second phase separation, either the decrease of label on the solid phase or the label which has passed into the liquid phase. preferred for radioactive labellings and for colour and fluorescent labellings.

The process according to the present invention can, in principle, be applied at all sandwich test systems. The only prerequisite is a measurable back dissociation of the labelled first receptor after separation of the non-bound first receptor remaining in the liquid phase.

The peripheral conditions of the process according to the present invention are such that readily measurable back dissociations occur with and without the hook effect.

Figure 2:
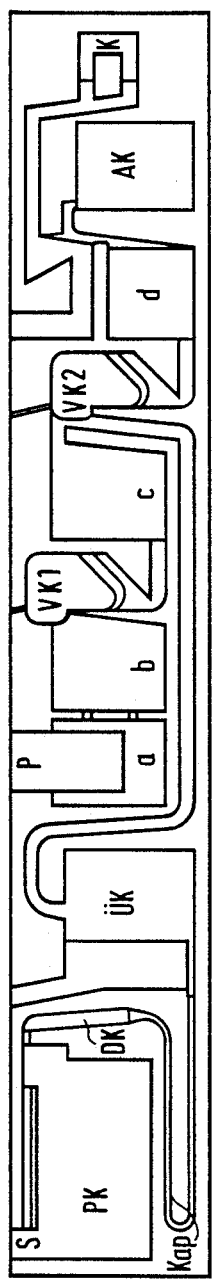

The following Examples are given for the purpose of illustrating the present invention, reference thereby being made to the accompanying drawings, in which:

FIG. 1 is a graphic representation of the dependency of the extinction (measurement value) upon the concentration of the analyte, the heavily marked part of the curve representing the calibration curve for the concentration determination of the analyte; and FIG. 2 illustrates an insert element for a centrifugal automatic analyser which can be used for carrying out the process according to the present invention.

EXAMPLE 1

Determination of AFP

Preparation of the reagent solutions

Substrate buffer 70 mmole/litre HEPES/NaOH (pH 7.0)
154 μmole/litre sodium chloride
5 g./litre bovine serum albumin
5 mmole/litre chlorophenol red $\beta$-galactoside (prepared according to Federal Republic of Germany Patent Specification No. 33 45 748)
2 g./litre Tween 20 (non-ionic detergent)

Receptor 1 solution

As receptor 1 solution, there is used a monoclonal mouse anti-AFP antibody which recognises an antigenic determinant different from that recognised by receptor 3. An ascites liquid containing this antibody is mixed ad 1.8 M/litre with ammonium sulphate. The precipitate is taken up in 15 mM/litre sodium phosphate buffer (pH 7.0) containing 50 mM/litre sodium chloride. The solution so obtained is subjected to a passage over DEAE-cellulose. The complete antibody is split up in known manner into Fab fragments. The Fab fragments obtained are coupled with $\beta$-galactosidase according to the method of E. Ishikawa, J. of Immunoassay, 4 (1983), S. 209–327.

(3) Receptor 2 solution

Sheep anti-mouse Fcγ antiserum is, as described above under 2), purified and also subjected to a passage over DEAE-cellulose.

(4) Receptor 3 solution

As receptor 3, there is used a monoclonal mouse anti-AFP antibody which recognises a determinant other than that recognised by receptor 1. An ascites liquid containing this antibody is mixed ad 1.8 mole with ammonium sulphate. The precipitate is taken up in 15 mmole/litre sodium phosphate buffer (pH 7.0) containing 50 mMole/litre sodium chloride, solution thus obtained is subjected to a passage over DEAE-cellulose.

(B) Preparation of the reagent carriers (1) Reagent carrier 1

(1) 40 μl. of a solution which, per litre, contains 100 mMole sodium phosphate (pH 7.3; 37° C.), 2 mMole magnesium chloride, 9 g. sodium chloride, 5 g. bovine serum albumin, 5 mg. anti-AFP monoclonal antibody from mice (receptor 3 solution) and 2000 U anti-AFP antibody (mouse) Fab fragment $\beta$-galactosidase conjugate (receptor 1 solution); activity determined with o-nitrophenyl-$\beta$-galactosodase at 37° C., is applied dropwise to a fleece which consists of commercially available polyester paper. It is subsequently dried at ambient temperature. This fleece is stored at 4° C. and at a relative atmospheric humidity of 20% until it is used.

(2) Reagent carrier 2:

On to a cellulose fleece, after cyanogen bromide activation (see Federal Republic of Germany Patent Specification No. 17 68 512), there are fixed sheep antibodies against the Fcγ part of mouse antibodies (receptor 2 solution), whereby, per g. of fibre material, here are made available for fixing 10 μg. of antibody. Uncoupled antibody is removed by washing and the fleece is gently dried at ambient temperature. The fleece thus obtained is stored analogously to reagent carrier 1.

The determination with the help of these two reagent carriers 1 and 2 takes place with the device described in Federal Republic of Germany Patent Specification No. 34 25 008 for the carrying out of analytic determinations (see FIG. 2). This describes a rotor insert element for a centrifugal automatic analyser which consists of a plurality of reagent fields in combination, each of which contains an absorbent carrier material impregnated with a particular reagent, at least one mixing valve chamber and a measurement chamber which together form a sample liquid transport path which passes from radially inwardly to radially outwardly when the rotor insert element is fixed to the rotor and further has at least one further chamber for the reception of a liquid and a transport path which passes from this chamber to the measurement path and is at least in part identical with the sample liquid transport path. The sample liquid transport path thereby passes from a sample reception chamber (p) via a chamber (a) filled with an absorbent material containing buffer, a chamber (c) and a first valve chamber (Vkl) arranged between the chambers (a) and (c) to a second valve chamber (Vk2) and from this, via a chamber (d) and via a reception chamber (AK) to measurement chamber (K). For the reception of a second liquid, there is provided a substrate chamber constructed as a pump chamber (PK) which has a substrate application port (S); and which is connected with the second valve chamber (Vk2) via a dosing unit consisting of a dosing chamber (DK) and capillar (Kap) and an overflow chamber. FIG. 2 of the accompanying drawings shows schematically the rotor insert element used.

Reagent carrier 1 is placed on field (c) of the rotor insert element and reagent carrier 2 on field (d). 40 µl. of sample are thereby pipetted through an opening on the upper edge directly on to the field (a). The sample is diluted 1:5 (v/v) with 0,9% aqueous sodium chloride solution, 270 µl of substrate solution are pipetted into chamber PK. By means of an appropriate centrifuging programmed, in which high speeds of rotation alternate with stopping, the sample and the substrate solution are then conveyed in the direction of the separation matrix and cuvette.

In the course of the programmed, the receptors 1 and 3 are thereby eluted by the sample liquid from field (c) and the homogeneous mixture is subsequently brought to reaction. On field (d), the complex formed is bound to receptor 2. The transfer of the sample from field (c) to (d) takes place within a very short space of time.

The substrate solution is divided up by the dosing chamber DK into portions, the first of which serve for washing out excess, non-complexed conjugate. The β-galactosidase activity bound to (d) b, complex formation is proportional to the amount of AFP present in the sample. This activity is determined with a further portion of substrate, the substrate thereby being reacted in a 5 minute reaction to give coloured products. The colour formed and the further colour development/minute in the liquid phase are measured in the cuvette at 600 nm. Under these conditions, the following results have been obtained:

All measurements were carried out at 600 nm at a layer thickness of 0.3 cm. and recalculated to a layer thickness d=1cm.

EXAMPLE 2

IgE determination

The procedure described in Example 1 is used but with the following differences:
(a) as receptor 3, there is used a monoclonal mouse anti-IgE antibody directed against human IgE;
(b) as receptor 1, there is used a further monoclonal mouse anti-IgE antibody directed against IgE which, however, recognises an antigen determinant different from that recognised by receptor 3;
(c) in the preparation of reagent carrier 1, 12 mU/test of receptor 1 solution are used; and
(d) the sample is diluted 1:3 with aqueous sodium chloride solution.

Under the appropriate conditions, the following results were obtained:

| U/ml. | 0 | 52 | 90 | 182 | 278 | 383 | 489[1] | 12,200[1] | 29,750 | 64,500 | 118,000 |
|---|---|---|---|---|---|---|---|---|---|---|---|
| measurement value (mE) | 88 | 604 | 1098 | 2050 | 2898 | 3646 | 4073 | 6445 | 4573 | 3151 | 2230 |
| increase[2] (mE/min) | 4 | 34 | 60 | 101 | 127 | 146 | 150 | 68 | 65 | 98 | 38 |
| $\alpha = \frac{\text{increase}}{\text{measurment value}} \times 100$ | 4.5 | 5.6 | 5.5 | 4.9 | 4.4 | 4.0 | 3.7 | 1.1 | 1.4 | 1.5 | 1.7 | hook effect

[1] at concentrations from about 500 to 12,000 U/ml., the photometer measurement range was exceeded
[2] all measurements took place at 600 nm with a 0.3 cm. cuvette and the extinctions were subsequently recalculated to a 1 cm. light path The last three columns show values which are brought about by the hook effect and cannot be used for a quantitative determination of the analyte.

EXAMPLE 3

Microtiter plates (MTPs) are coated, per cup, with 200 µl. of a solution of a monoclonal mouse anti-AFP antibody receptor 2 solution in a concentration of 1 µg. of protein/ml. in buffer A (20 mM carbonate buffer (pH 9.6)) for 1 hour at ambient temperature. Subsequently, non-specific binding phases are saturated by post-incubation of the MTPs with 300 µl. of buffer B (50 mM potassium phosphate buffer (pH 7.5), 154 mM sodium chloride, 1bovine serum albumin and 1 g./litre Tween 20) for 30 minutes at ambient temperature.

| IU/ml. | 0 | 60 | 135 | AFP 200 | 50,000 | 100,000 | 200,000 | 500,000 | 1,000,000 |
|---|---|---|---|---|---|---|---|---|---|
| measurement value (mE) | 274 | 1516 | 2783 | 5363 | >8.000 | 6587 | 4670 | 2782 | 2069 |
| increase $\left(\frac{mE}{min}\right)$ | 19 | 131 | 217 | 305 | — | 48 | 40 | 30 | 32 |
| $\alpha =$ increase/measurement value × 100 | 6.9 | 8.6 | 7.8 | 5.7 | — | 0.7 | 0.9 | 1.1 | 1.5 | hook effect

After washing with 300 μl. of buffer C (100 mM HEPES/NaOH (pH 7.25), 154 mM sodium chloride, 2.5 g./litre sheep normal IgG, 0.5 mM magnesium L-aspartate and 2 g./litre Tween 20), there are introduced. per cup, 50 μl. of sample and 200 l of an enzyme-antibody conjugate (receptor 1 solution; β-galactosidase conjugate of a Fab fragment from a further monoclonal mouse anti-AFP antibody which does not hinder antibody from receptor 2: 0.5 U/ml.: measurement of the activity with o-nitrophenyl-β-D-galactoside at 37°) in buffer C and incubated for 1 hour at ambient temperature. Subsequently, the liquids are discarded from the MTP cups, the cups are washed with 300 μl. buffer B and thereafter incubated with 250 μl. of substrate solution (5 mM chlorophenol red μ-D-galactoside, 70 mM HEPES/NaOH (pH 7.0), 154 mM sodium chloride, 3 /litre bovine serum albumin and 2 g./litre Tween 20) for 2.5 hours at ambient temperature.

After the epiry of this incubation time, 100 μl. are removed from each cup of the MTP and transferred to the cups of a further MTP. Immediately thereafter, there takes place an absorption measurement (measurement $t_1$) by means of a commercially available MTP measurement apparatus (=570 nm, bichromic correction at 630 nm) and after a further incubation period of 1 hour at ambient temperature there takes place a second absorption measurement (measurement $t_2$) under the same conditions as measurement $t_1$. The absorption difference between measurement $t_1$ and measurement $t_2$ is proportional to the amount of enzyme transferred with the substrate solution. The results of a typical experiment are given in the following Table:

| (AFP) in IU/ml | 1.5 | 10 | 40 | 156 | 625 | 2,500 | 10,000 | 40,000 |
|---|---|---|---|---|---|---|---|---|
| $mE_{t1}$ | 67 | 419 | 1720 | >(2) | >(2) | >(2) | 1643 | 485 |
| $mE_{t2} - mE_{t1}$ | 32 | 171 | 540 | — | — | — | 141 | 51 |
| $\alpha^{(1)}$ | 478 | 408 | 314 | — | — | — | 86 | 105 |

The last two columns show the presence of a hook effect.

(1)

$$\alpha = \frac{mE_{t2} - mE_{t1}}{mE_{t1}} \times 100$$

(2) above the photometer measurement range (2000 mE).

I claim:

1. Process for determining if the Hook effect occurs in an analyste containing liquid sample, comprising incubating an analyte containing sample with a labeled first receptor which binds to said analyte and a second, solid phase bound receptor which is not cross reactive with said first receptor and which binds to complex containing said first receptor and analyte, separating liquid phase from solid phase, measuring label bound to said solid phase at a first time after said liquid phase is separated therefrom, and at a further time after the first measurement the back dissociation velocity of said labeled first receptor is determined, and relating said back dissociation value for said sample to a control back dissociation value, wherein a decrease in back dissociation value for said sample as compared to said control is an indication of the occurrence of the Hook Effect.

2. Process of claim 1, wherein said further measurement comprises measuring label bound to the solid phase.

3. Process of claim 1, wherein said solid phase bound receptor binds to said complex of first receptor and analyte to form a three member solid phase receptor-analyte-receptor complex, said process comprising contacting said three member complex with a solution of a color forming reagent, removing said reagent solution, and determining said back dissociation value by taking said first and said further measurement in said reagent solution.

4. Process of claim 1, further comprising contacting said solid phase with a wash solution after taking said first measurement and taking said further measurement in either said solid phase or said wash solution.

5. Process of claim 1, further comprising adding a third receptor which specifically binds to a determinant of said analyte which is different from the receptor to which said first receptor binds wherein said second and third receptors bind with each other.

6. Process of claim 5, wherein said third receptor is a monoclonal antibody, said first receptor is a Fab fragment of a monoclonal antibody, and said second receptor binds to the Fc portion of said third receptor.

7. Process of claim 1, wherein said first and further measurements are taken over a time interval ranging from about 20 seconds to about 60 minutes.

8. Process of claim 1 wherein at least one of said receptors is selected from the group consisting of protein A, immunoglobulin G, avidin, biotin, concanavalin A and lectin.

* * * * *

UNITED STATES PATENT AND TRADEMARK OFFICE
CERTIFICATE OF CORRECTION

PATENT NO. : 4,966,839  
DATED : October 30, 1990  
INVENTOR(S) : Klaus Peter Kaspar It is certified that error appears in the above-identified patent and that said Letters Patent is hereby corrected as shown below:

Column 2, line 18: change "lining" to -- binding --.

Column 5, line 21: before "preferred" add -- This embodiment is especially --;

line 52: change "7/8" to -- $\beta$ --.

Column 6, line 16: change "chloride, solution" to -- chloride. The solution --;

line 41: change "here are made" to -- there are made --.

Column 7, line 6: change "capillar" to -- capillary --;

line 16: change "programmed" to -- programme --;

line 44: change "b, complex" to -- by complex --.

UNITED STATES PATENT AND TRADEMARK OFFICE
CERTIFICATE OF CORRECTION

PATENT NO. : 4,966,839

DATED : October 30, 1990

INVENTOR(S) : Klaus P. Kaspar

It is certified that error appears in the above-identified patent and that said Letters Patent is hereby corrected as shown below:

Column 8, line 49: change "1bovine" to -- 1% bovine --.

Column 9, line 16: change "red $\mu$-D" to -- red $\beta$-D --;

line 21: change "epiry" to -- expiry --.

Signed and Sealed this

Twenty-second Day of September, 1992

Attest:

DOUGLAS B. COMER

*Attesting Officer*  *Acting Commissioner of Patents and Trademarks*